United States Patent [19]

Vick et al.

[11] 4,345,088
[45] Aug. 17, 1982

[54] PREPARATION OF ALKOXYAMINOHYDRIDOSILANES

[75] Inventors: Steven C. Vick, Stormville; Bernard Kanner, West Nyack, both of N.Y.

[73] Assignee: Union Carbide Corporation, Danbury, Conn.

[21] Appl. No.: 249,442

[22] Filed: Mar. 31, 1981

[51] Int. Cl.³ ............................................. C07F 7/10
[52] U.S. Cl. .................................................. 556/410
[58] Field of Search ........................................ 556/410

[56] References Cited

U.S. PATENT DOCUMENTS

| | | | |
|---|---|---|---|
| 2,566,363 | 9/1951 | Pedlow et al. | 556/410 |
| 2,724,698 | 11/1955 | Kittleson | 556/410 X |
| 3,030,403 | 4/1962 | Pike | 556/410 X |
| 3,054,818 | 9/1962 | Pepe et al. | 556/410 |
| 4,237,172 | 12/1980 | Packo et al. | 428/63 |

OTHER PUBLICATIONS

Noll, "Chemistry and Technology of Silicones", Academic Press, N.Y. (1968), p. 107.
Eaborn, *Organosilicon Compounds*, Academic Press Inc., N.Y. (1960), p. 344.

*Primary Examiner*—Paul F. Shaver
*Attorney, Agent, or Firm*—Paul W. Leuzzi, II

[57] ABSTRACT

Novel compounds of the formula

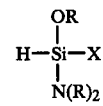

are produced by reacting tris(dialkylamino)hydridosilanes with alkanols under specified conditions. The novel compounds are useful as analytical tools, as coupling agents, and in organic synthesis.

24 Claims, No Drawings

PREPARATION OF ALKOXYAMINOHYDRIDOSILANES

BACKGROUND OF THE INVENTION

1. Field of the Invention

This invention relates to novel silicon-containing organic chemical compounds which are alkoxyaminohydridosilanes of the formula

wherein X is OR or N(R)$_2$.

2. Description of Relevant Art

Both trialkoxyhydridosilanes and tris(dimethylamino)hydridosilane have been known for some time. Eaborn, *Organosilicon Compounds*, Academic Press Inc., N.Y., 1960, at page 344 discloses di-primaryamino-di-tertiarybutoxysilane, a compound which contains no hydrogen bonded to silicon.

U.S. Pat. No. 4,237,172 describes the preparation of "most preferred" methylbis(dimethylamino)hydridosilane from methyldichlorohydridosilane and dimethylamine. The patent also contains some generic language which seems to embrace the monoalkoxybis(dialkylamino)hydridosilanes and dialkoxymono(dialkylamino)hydridosilanes of the present invention, but they are not mentioned specifically and, in any event, the patent does not adequately teach those skilled in the art how to prepare them.

U.S. patent application Ser. No. 163,976, which was filed on June 30, 1980, discloses the preparation of tetraalkoxysilanes by a synthetic route which comprises first contacting alkanol and dimethylamine with copper-activated silicon metal and then adding alkanol to the resulting silane mixture. While it is possible that the intermediate silane mixture might contain, inter alia, some molecules which correspond to the compounds claimed herein, the synthetic route which is the subject of the cited application clearly does not constitute a realistic method for their production.

It is believed that compounds containing an alkoxy group, a dialkylamino group, and a hydrogen atom all attached to a single silicon atom were, previous to the present invention, unknown.

SUMMARY OF THE INVENTION

This invention is directed to compounds of the formula

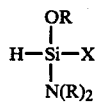

wherein X is OR or N(R)$_2$ and wherein R is alkyl of from one to eight carbon atoms, and to the preparation of such compounds from tris(dialkylamino)hydridosilanes.

DESCRIPTION OF THE PREFERRED EMBODIMENTS

The present invention provides alkoxyaminohydridosilanes, that is, compounds in which one silicon atom is bonded to an alkoxy group, to an amino group, and to a hydrogen atom. More specifically, the compounds contemplated by the present invention have the formula (RO)$_m$(R$_2$N)$_n$SiH, wherein m=1 or 2, n=1 or 2, m≠n, and R represents an alkyl group which has up to eight carbon atoms. Typical specific embodiments of the compounds provided by the present invention are those of the formulae:

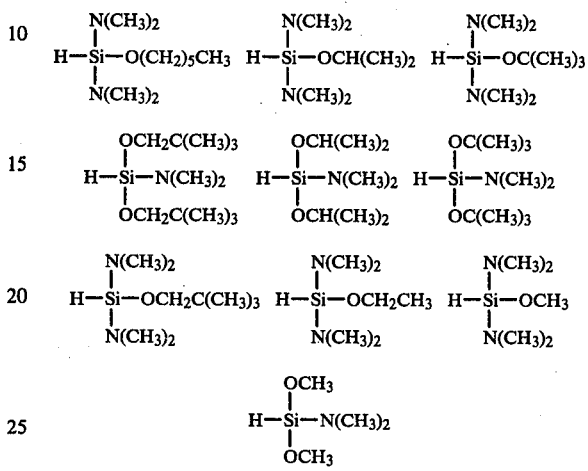

The compounds provided by the present invention are useful in many ways.

For instance, these compounds will react rapidly and quantitatively with secondary alcohols at room temperature in the absence of catalysts, while under the same conditions, they will not react at all with tertiary alcohols. For this reason they constitute a valuable tool for use in the quantitative analysis of mixtures containing both secondary and tertiary alcohols. To so use them, one measures the total weight of both classes of alcohol in the sample to be analyzed, reacts the sample with an excess of one or more compounds according to the present invention, separates the unreacted tertiary alcohol from the reaction mixture, e.g. by distillation, measures the weight of the tertiary alcohol so separated, and calculates (by subtracting it from the total secondary and tertiary alcohol weight measurement) the weight of the secondary alcohol, thus providing separate quantitative analysis of the secondary and tertiary alcohol content of the mixture.

Other fields of usefulness of the compounds provided by the present invention derives from the fact that each compound has three different types of reactivity, arising from the Si-OR linkage, the Si-N linkage, and the Si-H linkage. This triple reactivity provides a versatility which is of value in fields ranging from the silane coupling agent art, where they may be used in the same manner as conventional organofunctional silanes to improve the mechanical properties of filled resins, to the pharmaceutical industry, where they may be used analogously to known aminosilanes in the synthesis of antibiotics such as penicillins.

The alkoxyaminohydridosilanes of the present invention all can be prepared by a process which comprises reacting tris(dialkylamino)hydridosilane with alkanol. However, the reactivity of the alkanol with tris(dialkylamino)hydridosilane varies so greatly, depending in large part upon whether the alkanol is primary, secondary, or tertiary, that different sets of processing conditions are necessary for the different types of alkanol.

Alkanols may be characterized as primary, secondary, or tertiary, depending on whether the carbon atom attached to the hydroxyl radical is itself attached to hydrogen or one, two, or three carbon atoms, respectively. Primary alkanols may be represented by the formula $HO\text{-}CH_2R^1$, wherein $R^1$ represents hydrogen or an alkyl group. Secondary alkanols may be represented by the formula $HO\text{-}CHR^1R^2$, wherein $R^1$ and $R^2$ represent, independently, alkyl groups. Tertiary alkanols may be represented by the formula $HO\text{-}CR^1R^2R^3$, wherein $R^1$, $R^2$, and $R^3$ represent, independently, alkyl groups.

Primary alkanols, in less than equivalent ratios, actually react so readily and fast with tris(dimethylamino)hydridosilane that they form, almost instantaneously, at room temperature and in the absence of catalyst, a mixture of trialkoxyhydridosilanes, tetraalkoxysilanes, and unreacted tris(dimethylamino)hydridosilane. In order to favor the formation of trialkoxysilanes, substantially less than equivalent ratios of the primary alkanol must be used. When a 3:1 molar ratio (which is a 1:1 equivalent ratio) of primary alkanol to tris(dimethylamino)hydridosilane is used, the predominant components of the uncatalyzed reaction product are tetraalkoxysilane and unreacted tris(dimethylamino)hydridosilane. To prepare compounds according to the present invention wherein the alkoxy radicals are derived from primary alkanols, one actually effects a redistribution reaction by reacting the tris(dimethylamino)hydridosilane with the primary alkanol in the presence of a Lewis acid catalyst and at an elevated temperature, i.e. at least about 50° C. and preferably at reflux. Alternatively, one may prepare the primary alkoxy compounds, according to the present invention where the trialkoxyhydridosilane is obtained from a source other than the in situ instantaneous reaction by mixing it with the tris(dialkylamino)hydrosilane and effective redistribution in situ with the Lewis acid catalyst and elevated temperature.

In the cases of secondard and tertiary alkanols, no such in situ redistribution is necessary. Where the alkanol is secondary, the desired alkoxyaminohydridosilanes may be prepared simply by reacting the appropriate alkanol with the appropriate tris(dialkylamino)hydridosilane at ambient temperature (in the absence of catalyst). Where the alkanol is tertiary, the reaction is carried out at an elevated (at least 50° C. and, usually, reflux) temperature in the presence of a catalytic amount of Lewis acid. In the absence of catalyst, no reaction of tertiary alkanol with tris(dialkylamino)hydridosilane takes place.

In most cases, where it is desired to favor the preparation of monoalkoxybis(dialkylamino)hydridosilane, the molar ratio of alkanol to tris(dialkylamino)hydridosilane to be utilized should be close to 1:1, and where it is desired to favor the preparation of dialkoxymono(dialkylamino)hydridosilane, the molar ratio of alkanol to tris(dialkylamino)hydridosilane to be utilized should be close to 2:1. Those skilled in the art will readily determine the ratio necessary to achieve the product distribution desired for any particular application.

The production of compounds according to the present invention by the procedures outlined above result in the preparation of reaction mixtures from which the desired compounds can be separated by conventional techniques, such as distillation. The compounds can generally be separated from each other, except in those cases where their boiling points are too close. In any event, they can be used as mixtures in such previously described applications as analytical tools and coupling agents.

The following Examples illustrate the preparation of alkoxyaminohydridosilanes according to the present invention. Each Example describes the reaction of tris(dimethylamino)hydrosilane with an alkanol as indicated. In the Examples, the abbreviation "glc" denotes gas liquid chromatography.

EXAMPLE 1

Reaction with n-Hexanol

A one hundred milliliter round bottom flask, equipped with a reflux condenser, magnetic stirrer, and thermometer was charged with 8.76 grams (54.3 millimoles) of tris(dimethylamino)hydridosilane and with about one-tenth of one gram of aluminum trichloride. Then 5.65 grams (55.3 millimoles) of n-hexanol was added dropwise by syringe with continuous stirring. The mixture was heated to and maintained at reflux temperature for two hours. Glc yield analysis showed that 44.1% (23.9 millimoles) of the tris(dimethylamino)hydridosilane was converted to mono-n-hexoxybis(dimethylamino)hydridosilane and that 6.3% (3.4 millimoles) was converted to di-n-hexoxymono(dimethylamino)hydridosilane.

$HSi[O(CH_2)_5CH_3](NMe_2)_2$ Characterization

IR (neat film): 2960(sh), 2940(s), 2870(s), 2850(sh), 2800(m), 2120(m), 1490(w), 1460(m), 1385(w), 1300(s), 1185(s), 1090(m), 1070(sh), 995(s), 880(m), 835(m), 630(w) cm$^{-1}$ nmr (benzene-$d_6$/benzene): $\delta$ 0.86–1.94(complex mult, 11H, maxima at 1.08, 1.43, 1.53, 1.63, C-CH), 2.76(S, 12H, NMe$_2$) 3.90 (t, 2H, J=6 Hz, OCH$_2$), 4.82(S, 1H, SiH) ppm Mass Spec: m/e (rel. intensity): 219(M$^+$ +1, 5), 218(M$^+$,24), 203(M$^+$-15, 6), 174(M$^+$-44, 22), 161(15), 147(11), 144(20), 135(13), 133(19), 132(10), 131(10), 130(13), 119(28), 118(15), 117(M$^+$-101, 43), 116(16), 92(26), 90(91), 89(10), 88(12), 76(12), 74(52), 73(12), 72(28), 58(11), 55(19), 47(10), 46(18), 45(22), 44(86), 43(83), 42(45), 41(94).

$HSi[O(CH_2)_5CH_3]_2NMe_2$ Characterization

IR (neat film): 2960(sh), 2930(s), 2870(s), 2800(m), 2160(m), 2120(sh), 1480(sh), 1465(m), 1455(sh), 1440(sh), 1385(w), 1300(m), 1180(m), 1115(sh), 1080(s), 1075(sh), 1040(sh), 995(s), 955(m), 800(s), 855(sh), 840(sh), 720(w) cm$^{-1}$ Nmr (benzene-$d_6$/benzene): $\delta$ 0.90–2.10(complex mult, 22H, maxima at 1.10, 1.45 and 1.55, C-CH), 2.75(S, 6H, NMe$_2$), 4.00(t, 4H, J=5.5 H$_z$, OCH$_2$), 4.88 (S, 1H, SiH) ppm Mass spec.=m/e (rel. intensity) 275(M$^+$,43), 260(M$^+$-15,11), 247(12), 246(53), 233(14), 232(35), 219(12), 218(19), 204(15), 197(10), 193(22), 192(84), 190(34), 177(18), 176(19), 174(M$^+$-101, 22), 168(14), 162(21), 152(13), 151(10), 150(32), 148(17), 142(17), 139(10), 137(24), 136(35), 128(13), 90(62), 89(14), 88(12), 87(13), 86(10), 85(18).

EXAMPLE 2

Reaction with Ethanol

A one hundred milliliter round bottom flask, equipped with a reflux condenser, magnetic stirrer, and thermometer was charged with 5.78 grams (35.8 millimoles) of tris(dimethylamino)hydridosilane followed by dropwise addition of 1.65 grams (35.8 millimoles) of ethanol. A slight exotherm was observed. After the addition was complete, the reaction mixture was cooled to room temperature. Approximately one-tenth of one gram of aluminum chloride was added to the reaction mixture, which was then stirred for about twelve hours. The reaction mixture was then heated to reflux temperatures (80°–120° C.) for six hours, with stirring, and subsequently allowed to cool to room temperature. Yield analysis (approximated by glc area % equals weight %) showed that 32.5% (11.6 millimoles) of the tris(dimethylamino)hydridosilane was converted to monoethoxybis(dimethylamino)hydridosilane and that 3.9% (1.4 millimoles) was converted to diethoxymono(dimethylamino)hydridosilane.

HSi(OEt)(NMe$_2$)$_2$ Characterization mass spec: m/e (relative intensity) 163 (M$^+$+1, 25), 162 (M$^+$, 100) 147 (M$^+$-15, 30), 119 (48), 118 (M$^+$-44, 68), 117 (15), 116 (33), 104 (32), 103 (10), 90 (32), 89 (11), 75 (24), 74 (91), 73 (30), 72 (26), 58 (13), 44 (55).

EXAMPLE 3

Reaction with Neopentanol

A one hundred milliliter round bottom flask, equipped with a reflux condensor, magnetic stirrer, and thermometer was charged with 14.05 grams (87.1 millimoles) of tris(dimethylamino)hydridosilane and, dropwise, 7.53 grams (85.4 millimoles) of neopentanol. Approximately one-tenth of one gram of aluminum trichloride was then added, and the reaction mixture was maintained at 60°–75° C. for one-half hour. Glc yield analysis showed that 10.6% (9.20 millimoles) of the tris(dimethylamino)hydridosilane was converted to mononeopentoxybis(dimethylamino)hydridosilane and that 13.4% (11.68 millimoles) was converted to dineopentoxymono(dimethylamino)hydridosilane.

HSi—OCH$_2$C(CH$_3$)$_3$](NMe$_2$)$_2$ Characterization

IR (neat film): 2960(s), 2890(sh), 2870(s), 2850(sh), 2800(s), 2760(sh), 2730(w), 2125(s), 1480(m), 1465(m), 1450(sh), 1400(w), 1365(m), 1300(s), 1240(w), 1185(s), 1150(w), 1080(s), 1030(w), 990(s), 880(s), 840(s), 700(w), 640(w), cm$^{-1}$ Nmr (benzene-d$_6$/benzene): δ 1.20(s, 9H, C-CH$_3$), 2.75(S, 12H, NMe$_2$), 3.60(S, 2H, O-CH$_2$), 4.80(S, 1H, Si-H) ppm Mass spec: m/e (rel. intensity) 205(M$^+$+1, 2), 204(M$^+$, 12), 189(M$^+$-15, 7), 160(M$^+$-44, 18), 117(M$^+$-87, 22), 90(35), 74(29), 72(16), 58(13), 57(100), 56(13), 55(27), 46(14), 45(22), 44(57), 43(30), 42(48), 41(87).

Hsi—OCH$_2$C(CH$_3$)$_3$]$_2$ NMe$_2$ Characterization

IR (neat film): 2960(s), 2900(s), 2880(s), 2800(m), 2170(m), 1480(m), 1470(sh), 1455(sh), 1400(m), 1365(m), 1300(m), 1265(w), 1220(m), 1185(m), 1080(s), 1030(m), 1000(s), 935(sh), 915(m), 880(s), 865(sh), 800(sh), 665(w), cm$^{-1}$ Nmr (benzene-d$_6$/benzene): δ1.20(S, 18H, C-CH$_3$), 2.75(S, 6H, NMe$_2$), 3.65(S, 4H, O-CH$_2$), 4.85(S, 1H, Si-H) ppm Mass spec: m/e (rel. intensity) 248(M$^+$+1, 6), 247(M$^+$, 31), 246(11), 232(M$^+$-15, 100), 191(13), 190(11), 176(41), 162(22), 160(M$^+$-87, 14), 120(15), 106(27), 90(87), 71(11), 63(12), 58(11), 57(90), 55(16), 44(41), 43(28), 41(60),

EXAMPLE 4

Reaction with Isopropanol

A one hundred milliliter round bottom flask, equipped with a reflux condensor, magnetic stirrer, and thermometer was charged with 15.64 grams (97.0 millimoles) of tris(dimethylamino)hydridosilane. This was followed by the dropwise addition of 5.73 grams (95.3 millimoles) of isopropanol. No catalyst was added to the reaction mixture. The reaction mixture was heated to reflux (84° C.) and maintained at reflux for one-half hour. Identification of the products was based on their mass spectra and relative glc retention times. An approximate yield analysis based upon glc peak area indicated that about 50% of the tris(dimethylamino)hydridosilane was converted to monoisopropoxybis(dimethylamino)hydridosilane and that about 25% was converted to diisopropoxymono(dimethylamino)hydridosilane.

HSi—O-CH(CH$_3$)$_2$](NMe$_2$)$_2$ Characterization

This spectrum was obtained by subtracting the mass spec for TRIS from the obtained spectrum.

Mass spec: m/e (rel. intensity), 176(M$^+$, not observed), 161(M$^+$-15, 60), 117 (M$^+$-59, 47), 74(74), 72(33), 45(14), 44(66), 43(12), 42(61).

HSi—O-CH(CH$_3$)$_2$]$_2$NMe$_2$ Characterization

Mass spec: m/e (rel. intensity) 192(M$^+$+1, 2), 191(M$^+$, 14), 149(11), 63(29), 45(18), 43(100), 42(12), 41(44).

EXAMPLE 5

Reaction with t-Butanol

A one hundred milliliter round bottom flask, equipped with a reflux condensor, magnetic stirrer, and thermometer was charged with 9.91 grams (61.44 millimoles) of tris(dimethylamino)hydridosilane, 4.69 grams (63.28 millimoles) of t-butanol, and 0.19 gram of aluminum chloride. The mixture was heated to reflux and maintained at reflux for 45 minutes. Glc yield analysis showed that 39.6% (24.33 millimoles) was converted to mono-t-butoxybis(dimethylamino)hydridosilane and that 25.0% (15.34 millimoles) was converted to di-t-butoxymono(dimethylamino)hydridosilane. The mixed alkoxyaminohydridosilanes were identified on the basis of the following:

Hsi—O-C(CH$_3$)$_3$](NMe$_2$)$_2$ Characterization

IR (neat film): 2980(s), 2880(sh), 2870(s), 2840(s), 2800(s), 2130(s), 1490(w), 1460(m), 1390(w), 1365(m), 1300(s), 1240(m), 1200(sh), 1185(s), 1140(sh), 1045(s), 1020(s), 995(s), 890(s), 840(s), 810(w), 705(m), 630(w), cm$^{-1}$ Nmr (benzene d$_6$/benzene): δ 1.50(S, 9H, C-CH$_3$), 2.70(S, 12H, NMe$_2$), 4.90 (S, 1H, SiH) ppm Mass spec: m/e (rel. intensity) 191(M$^+$+1, 30), b 190(M$^+$, 100), 175(M$^+$-15, 61), 147(18), 146(M$^+$-44, 28), 145(17), 135(51), 134(50),133(100), 132(12), 120(24), 119(100), 117(M$^+$-73), 116(14), 105(17), 92(60), 91(100), 90 (100), 89(100), 88(56), 87(11), 76(60), 75(14), 74(100), 73(25), 72(85), 61(21), 59(21), 58(35), 57(55), 56(22), 47(44), 46(45), 45(96), 44(100), 43(72), 42(100), 41(100).

HSi—OC(CH$_3$)$_3$]$_2$NMe$_2$ Characterization

IR (neat film): 2980(s), 2940(sh), 2900(sh), 2870(m), 2850(sh), 2800(m), 2160(m), 1490(sh), 1460(m), 1390(m), 1365(s), 1300(m), 1240(m), 1190(s), 1045(s), 1020(s), 1000(s), 885(s), 860(s), 810(w), 690(w), 640(w) cm$^{-1}$ Nmr (benzene-d$_6$/benzene): δ1.60(S, 18H, C-CH$_3$), 2.75 (S, 6H, N-me$_2$), 4.95(S, 1H, SiH) ppm Mass spec: m/e (rel. intensity) 220(M+ +1, 7), 219(M+, 49), 164(29), 162(12), 148(96), 146(M+-73), 109(12), 108(100), 107(43), 106(100), 103(18), 90(97), 89(26), 88(12), 74(10), 72(10), 63(35), 59(16), 57(84), 45(20), 44(61), 43(23), 42(20), 41(69).

EXAMPLE 6

Reaction with t-Butanol

A one hundred milliliter round bottom flask, equipped with a reflux condensor, magnetic stirrer, and thermometer was charged with 10.65 grams (66.03 millimoles) of tris(dimethylamino)hydridosilane and 0.16 gram of aluminum chloride. This was followed by the dropwise addition of 9.85 grams (132.9 millimoles) of t-butanol. The mixture was heated to, and maintained at, reflux for one-half hour. Glc yield analysis showed that 9.7% (6.38 millimoles) was converted to mono-t-butoxybis(dimethylamino)hydridosilane and that 58.2% (38.4 millimoles) was converted to di-t-butoxymono(-dimethylamino)hydridosilane.

EXAMPLE 7

Reaction with Trimethoxyhydridosilane

A one hundred milliliter round bottom flask, equipped with a reflux condensor, magnetic stirrer, and thermometer was charged with 7.30 grams (45.3 millimoles) of tris(dimethylamino)hydridosilane, 0.1 gram of aluminum chloride, and 5.56 grams (45.5 millimoles) of trimethoxyhydridosilane. The mixture was heated to reflux (95°–100° C.) and maintained at reflux for five hours. Glc analysis revealed the presence of monomethoxybis(dimethylamino)hydridosilane and dimethoxymono(dimethylamino)hydridosilane.

The foregoing Examples are illustrative of the present invention. Those skilled in the art will readily conceive of other specific embodiments of the present invention, the scope of which is limited only by the following claims.

What is claimed is:

1. A compound of the formula

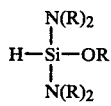

wherein each R represents an alkyl group of from one to eight carbon atoms.

2. A compound of the formula

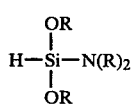

wherein each R represents an alkyl group of from one to eight carbon atoms.

3. A compound as in claim 1, having the formula

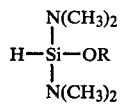

wherein R is an alkyl group of from one to eight carbon atoms.

4. A compound as in claim 2, having the formula

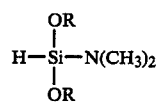

wherein R is an alkyl group of from one to eight carbon atoms.

5. A compound as in claim 3, having the formula

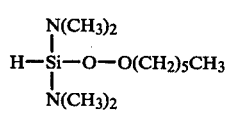

6. A compound as in claim 3, having the formula

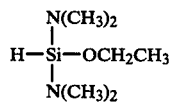

7. A compound as in claim 3, having the formula

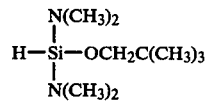

8. A compound as in claim 4, having the formula

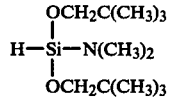

9. A compound as in claim 3, having the formula

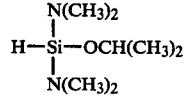

10. A compound as in claim 4, having the formula

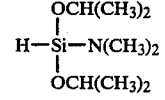

11. A compound as in claim 3, having the formula

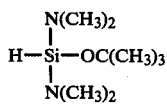

12. A compound as in claim 4, having the formula

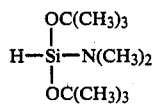

13. A compound as in claim 3, having the formula

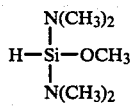

14. A compound as in claim 4, having the formula

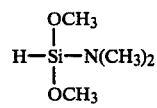

15. A process for producing a compound as in claim 1 or 2 wherein the alkoxy radicals are derived from primary alkanols which comprises reacting a compound of the formula

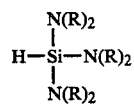

with a compound of the formula

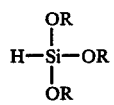

in the presence of a Lewis acid catalyst and at an elevated temperature.

16. A process as in claim 15 wherein the compound of the formula

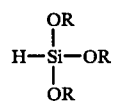

is produced in situ by reacting a tris(dialkylamino)hydridosilane compound of the formula

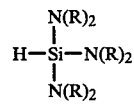

with a primary alkanol of the formula ROH.

17. A process according to claim 16 wherein the compound produced is

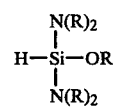

and wherein the molar ratio of the alkanol to the tris(dialkylamino)hydridosilane with which it is reacted is approximately 1:1.

18. A process according to claim 16 wherein the compound produced is

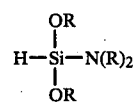

and wherein the molar ratio of the alkanol to the tris(dimethylamino)hydridosilane with which it is reacted is approximately 2:1.

19. A process for producing a compound as in claim 1 or 2 wherein the alkoxy radicals are derived from secondary alkanols which comprises reacting a tris(dialkylamino)hydridosilane compound of the formula

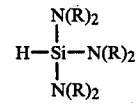

with a secondary alkanol of the formula ROH at ambient temperature in the absence of catalyst.

20. A process according to claim 19 wherein the compound produced is

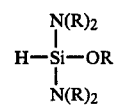

and wherein the molar ratio of the alkanol to the tris(dialkylamino)hydridosilane with which it is reacted is approximately 1:1.

21. A process according to claim 19 wherein the compound produced is

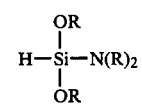

and wherein the molar ratio of the alkanol to the tris(dimethylamino)hydridosilane with which it is reacted is approximately 2:1.

22. A process for producing a compound as in claim 1 or 2 wherein the alkoxy radicals are derived from tertiary alkanols which comprises reacting a tris(dialkylamino)hydridosilane of the formula

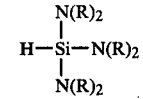

with a tertiary alkanol of the formula ROH in the presence of a Lewis acid catalyst and at an elevated temperature.

23. A process according to claim 22 wherein the compound produced is

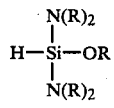
and wherein the molar ratio of the alkanol to the tris(-dialkylamino)hydridosilane with which it is reacted is approximately 1:1.
24. A process according to claim 22 wherein the compound produced is
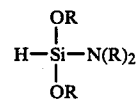
and wherein the molar ratio of the alkanol to the tris(-dimethylamino)hydridosilane with which it is reacted is approximately 2:1.
* * * * *

UNITED STATES PATENT AND TRADEMARK OFFICE
CERTIFICATE OF CORRECTION

PATENT NO. : 4,345,088
DATED : August 17, 1982
INVENTOR(S) : S. C. Vick and B. Kanner It is certified that error appears in the above—identified patent and that said Letters Patent is hereby corrected as shown below:

Column 3, line 37, please delete "effective" and insert therefor --effecting--.

Column 4, line 49, please delete "800(s)" and insert therefor --880(s)--.

In the Claims:

Claim 5, the formula should read:

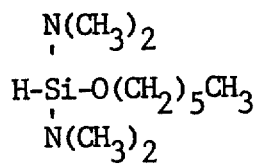

Signed and Sealed this

Seventeenth Day of May 1983

[SEAL]

Attest:

DONALD J. QUIGG

Attesting Officer — Acting Commissioner of Patents and Trademarks